(12) United States Patent
Ono et al.

(10) Patent No.: US 11,160,994 B2
(45) Date of Patent: Nov. 2, 2021

(54) PARTICLE BEAM THERAPY SYSTEM AND PARTICLE BEAM THERAPY METHOD

(71) Applicant: Hitachi, Ltd., Tokyo (JP)

(72) Inventors: Daisuke Ono, Tokyo (JP); Yuki Ito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 11 days.

(21) Appl. No.: 16/747,794

(22) Filed: Jan. 21, 2020

(65) Prior Publication Data

US 2020/0276454 A1 Sep. 3, 2020

(30) Foreign Application Priority Data

Feb. 28, 2019 (JP) .............................. JP2019-035886

(51) Int. Cl.
*A61N 5/10* (2006.01)

(52) U.S. Cl.
CPC .......... *A61N 5/1048* (2013.01); *A61N 5/1077* (2013.01); *A61N 2005/109* (2013.01);
(Continued)

(58) Field of Classification Search
CPC ...... A61N 5/1048; A61N 5/1064–1075; A61N 5/1077; A61N 5/10–1084;
(Continued)

(56) References Cited

U.S. PATENT DOCUMENTS

2012/0039294 A1 2/2012 Yan et al.
2014/0341195 A1 11/2014 Yan et al.
(Continued)

FOREIGN PATENT DOCUMENTS

CN 108348767 A 7/2018
JP 2010-82229 A 4/2010
(Continued)

OTHER PUBLICATIONS

Japanese Office Action received in corresponding Japanese Application No. 2019-035886 dated May 25, 2021.
(Continued)

*Primary Examiner* — Thaddeus B Cox
(74) *Attorney, Agent, or Firm* — Mattingly & Malur, PC

(57) ABSTRACT

The present invention makes it possible to reliably verify irradiation with a particle beam in accordance with a selected irradiation technique. A particle beam therapy system includes a charged particle beam generator accelerating the particle beam, an irradiator irradiating a target with the particle beam accelerated by the charged particle beam generator, and a controller controlling the charged particle beam generator and the irradiator. The controller controls the charged particle beam generator and the irradiator so as to irradiate the target with the particle beam through switching between at least two different irradiation techniques, and furthermore, after switching between the two irradiation techniques, controls the charged particle beam generator and the irradiator to perform tentative irradiation with the charged particle beam in accordance with one of the irradiation techniques switched, to verify the particle beam.

3 Claims, 11 Drawing Sheets

(52) U.S. Cl.
CPC ............... *A61N 2005/1074* (2013.01); *A61N 2005/1087* (2013.01)

(58) Field of Classification Search
CPC ...... A61N 2005/1087; A61N 2005/109; A61N 2005/1085–1098
See application file for complete search history.

(56) References Cited

U.S. PATENT DOCUMENTS

2017/0112457 A1\* 4/2017 Allinson .............. A61N 5/1077
2018/0326224 A1\* 11/2018 Umezawa ............ A61N 5/1043

FOREIGN PATENT DOCUMENTS

| | | |
|---|---|---|
| WO | 2010/124438 A1 | 11/2010 |
| WO | 2010/140236 A1 | 12/2010 |
| WO | 2017/081826 A1 | 5/2017 |

OTHER PUBLICATIONS

Chinese Office Action received in corresponding Chinese Application No. 202010013645.4 dated Aug. 30, 2021.

\* cited by examiner

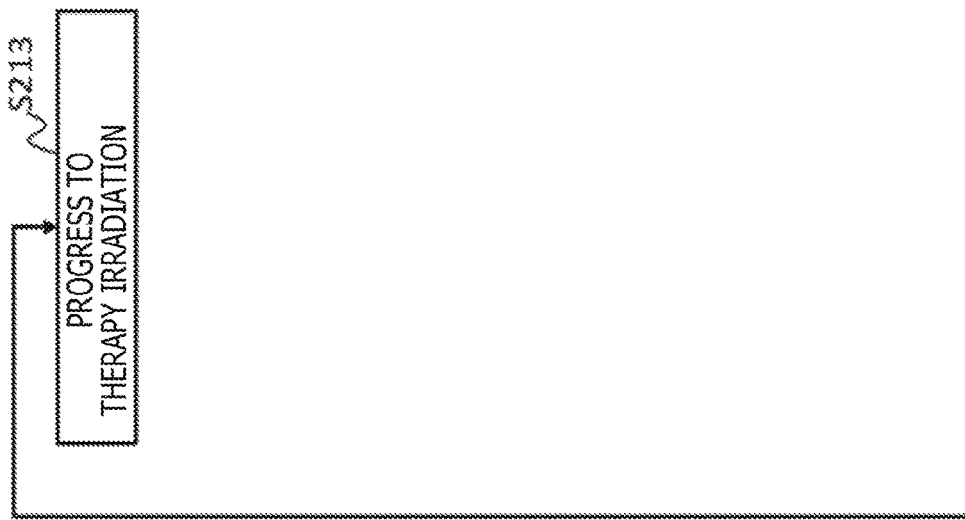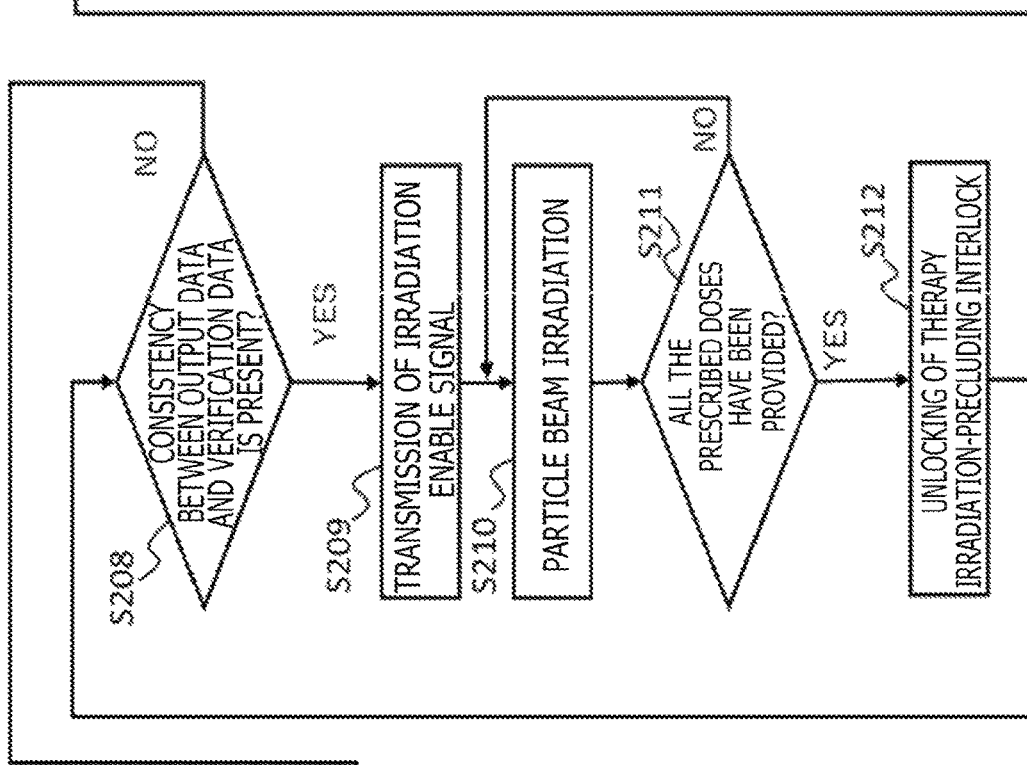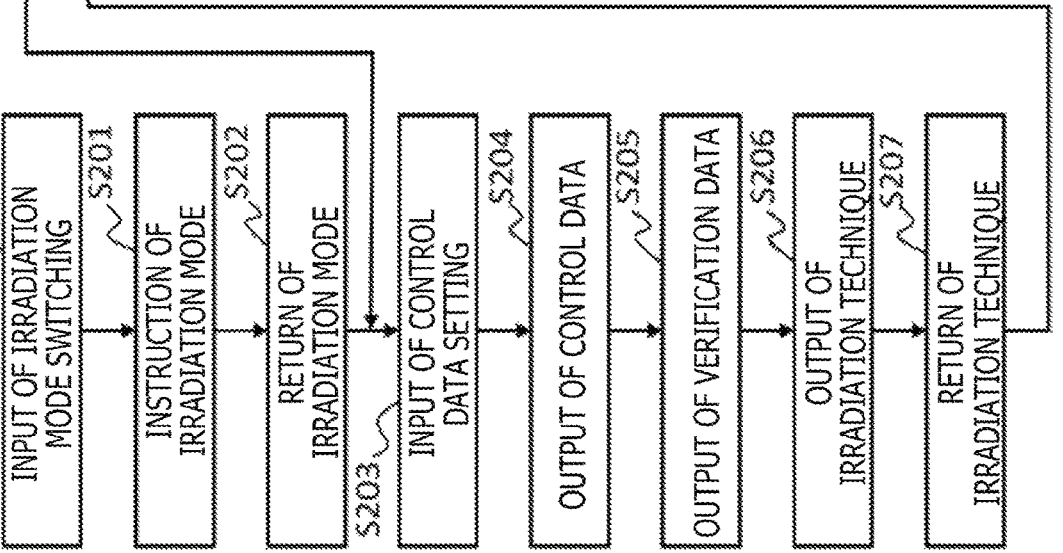
FIG. 7

PARTICLE BEAM THERAPY SYSTEM AND PARTICLE BEAM THERAPY METHOD

CROSS-REFERENCE TO RELATED APPLICATION

The present application claims priority from Japanese application JP 2019-035886, filed on Feb. 28, 2019, the contents of which is hereby incorporated by reference into this application.

BACKGROUND OF THE INVENTION

1. Field of the Invention

The present invention relates to a particle beam therapy system and a particle beam therapy method.

2. Description of the Related Art

As cancer radiotherapy, particle beam therapy is known in which a cancer-affected part of a patient is treated by irradiating the affected part with an ion beam such as protons and heavy ions.

For the particle beam therapy, a spot scanning method is known as a method in which a dose distribution with a thin beam is matched with a shape of an affected part and an ununiform and random dose distribution is formed. In this method, the shape of the affected part is divided into fine small regions, i.e. irradiation spots, and a desired irradiation dose is previously set for each division for irradiation.

The spot scanning method is roughly classified into two irradiation methods called a discrete spot scanning method and a raster scanning method. In the discrete spot scanning method, beam extraction is stopped while a position of a particle beam is moved from one irradiation spot to the next irradiation spot, and after completion of the movement, the beam extraction is restarted. In the raster scanning method, beam extraction continues unremittingly while scanning the same slice of an affected part.

WO2017/081826 discloses a particle beam therapy system, in which it is possible to select either the raster scanning technique or the discrete spot scanning technique depending on an affected part of a patient as an irradiation target on the basis of previous selection, and both the raster scanning technique and the discrete spot scanning technique can be executed by one irradiator.

SUMMARY OF THE INVENTION

In the raster scanning technique and the discrete spot scanning technique, besides a common control parameter set, a control parameter set used only in the raster scanning technique, or a control parameter set used only in the discrete spot scanning technique is used. The particle beam therapy system is controlled by switching the control parameter set in accordance with a selected irradiation technique.

For this reason, after switching between the raster scanning technique and the discrete spot scanning technique, it is necessary to verify whether the control parameter set has been correctly switched.

The present invention has been made in view of the above problem, and an object of the present invention is to provide a particle beam therapy system and a particle beam therapy method, which can reliably verify irradiation with a particle beam in accordance with a selected irradiation technique.

In order to solve the above problem, the particle beam therapy system according to one aspect of the present invention includes an accelerator accelerating a particle beam, an irradiator irradiating a target with the particle beam accelerated by the accelerator, and a controller controlling the accelerator and the irradiator. The controller controls the accelerator and the irradiator so as to irradiate the target with the particle beam through switching between at least two different irradiation techniques, and furthermore, after switching the irradiation technique, performs tentative irradiation with the particle beam by the accelerator and the irradiator in accordance with one of the irradiation techniques switched, to verify the particle beam.

The present invention makes it possible to reliably verify irradiation with a particle beam in accordance with a selected irradiation technique.

BRIEF DESCRIPTION OF THE DRAWINGS

FIG. 7 is a flowchart explaining operations of verification/adjustment irradiation in the particle beam therapy system according to the embodiment;

DESCRIPTION OF THE PREFERRED EMBODIMENTS

Hereinafter, an embodiment of the present invention will be explained with reference to drawings. Note that the embodiment explained below does not limit the invention according to claims, and all elements and combinations thereof explained in the embodiment are not necessarily essential for the means for solving the problem of the invention.

The particle beam therapy system according to the embodiment of the present invention uses a particle beam such as a proton beam or a carbon beam. The particle beam used in the particle beam therapy system according to the example is not limited as long as the particle beam is a particle beam which has already been practically used or will be practically used, such as the aforementioned proton beam and carbon beam.

Note that, when a term "data" is described in this specification, a number of "data" is not limited. Furthermore, a format of "data" is not limited. In addition, data or the like preserved or stored in what is generally called a table format in a memory medium is also referred to as the "data" described herein.

Figure 1:
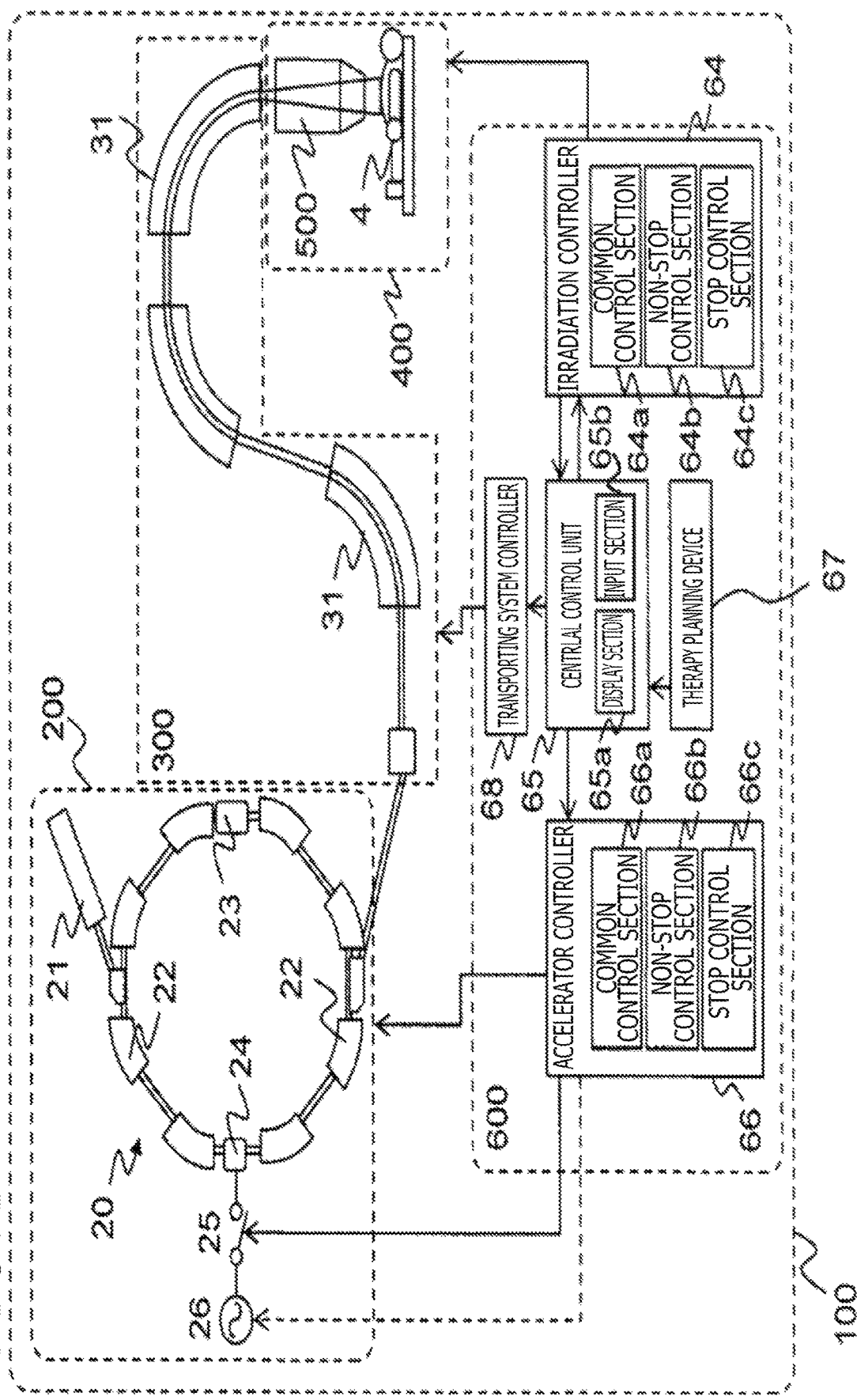
FIG. 1 is a schematic block diagram illustrating a particle beam therapy system according to an embodiment.

FIG. 1 is a schematic block diagram illustrating a particle beam therapy system according to the embodiment. A particle beam therapy system 100 according to the present embodiment includes a charged particle beam generator 200, a beam-transporting system 300 guiding the generated charged particle beam to a therapy room 400, an irradiator 500 performing irradiation with the charged particle beam in accordance with a shape of an affected part 41 illustrated in FIG. 2 of a patient 4 in the therapy room 400, and a controller 600.

The charged particle beam generator 200 includes a prestage accelerator 21, and a synchrotron 20 in which the charged particle beam previously accelerated by the prestage accelerator 21 is accelerated to predetermined energy and then extracted. Incidentally, instead of the synchrotron 20, an accelerator having no prestage accelerator such as a cyclotron, or a linear accelerator may be used.

The synchrotron 20 is a device in which the charged particle beam, for example, heavy particle ion such as proton and carbon, neutron, or the like, accelerated by the prestage accelerator 21 is accelerated to predetermined energy. The synchrotron 20 has a plurality of dipole magnets 22 and a plurality of quadrupole electromagnets not illustrated in drawings circulating the charged particle beam, an accelerator 23 accelerating the circulating charged particle beam, and an extraction device 24 extracting the charged particle beam accelerated to predetermined energy.

The extraction device 24 has a high-frequency applying electrode for extraction not illustrated in drawings. This high-frequency applying electrode is connected to a high-frequency power source 26 via an extraction switch 25, and switches on/off extraction of the charged particle beam depending on opening and closing of the extraction switch 25.

The beam-transporting system 300 includes a plurality of dipole magnets 31 and a plurality of quadrupole electromagnets not illustrated in drawings, and transports to the irradiator 500 the charged particle beam extracted from the synchrotron 20.

Figure 2:
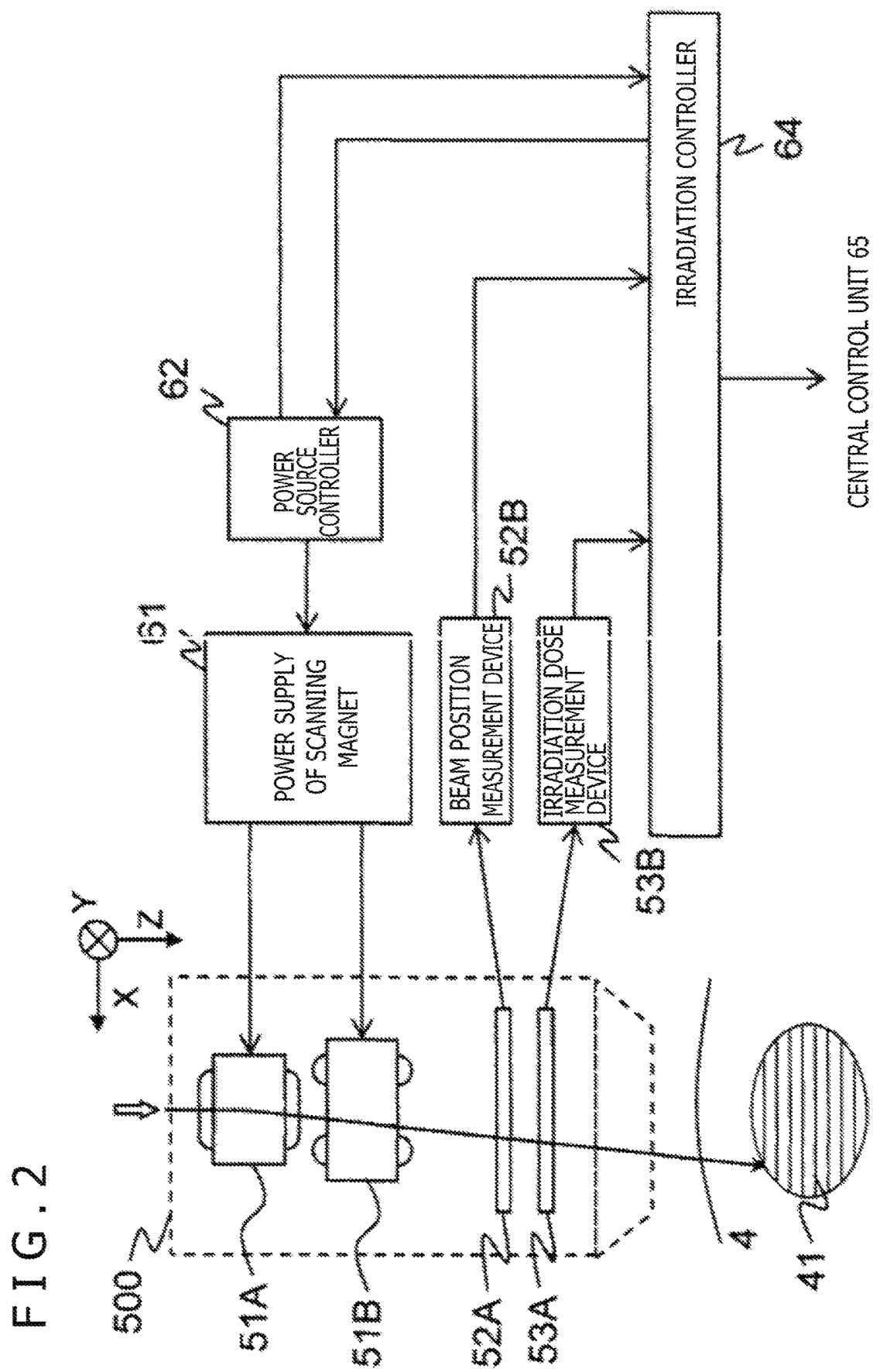
FIG. 2 is a diagram illustrating a configuration of an irradiator used for the particle beam therapy system according to the embodiment.

FIG. 2 is a diagram illustrating a configuration of the irradiator 500 used in the particle beam therapy system 100 according to the embodiment.

The irradiator 500 has an X-direction scanning magnet 51A and a Y-direction scanning magnet 51B, each of which horizontally, i.e. X direction in the figure, or vertically, i.e. Y direction in the figure and perpendicular to the paper face, scans the charged particle beam accelerated by the synchrotron 20 and guided by the beam-transporting system 300, and matches the beam with a shape of the affected part 41 of the patient 4. These scanning magnets 51A and 51B are connected to a power supply of scanning magnet 61. The power supply of scanning magnet 61 is controlled by a power source controller 62.

The charged particle beam deflected by the scanning magnets 51A and 51B passes through a beam position monitor 52A and a dose monitor 53A, and irradiates the affected part 41 as an irradiation target. The beam position monitor 52A is connected to a beam position measurement device 52B, and the beam position measurement device 52B measures a position and a width, i.e. extent, of the charged particle beam. The dose monitor 53A is connected to an irradiation dose measurement device 53B, and the irradiation dose measurement device 53B measures a dose of the charged particle beam.

Figure 3:
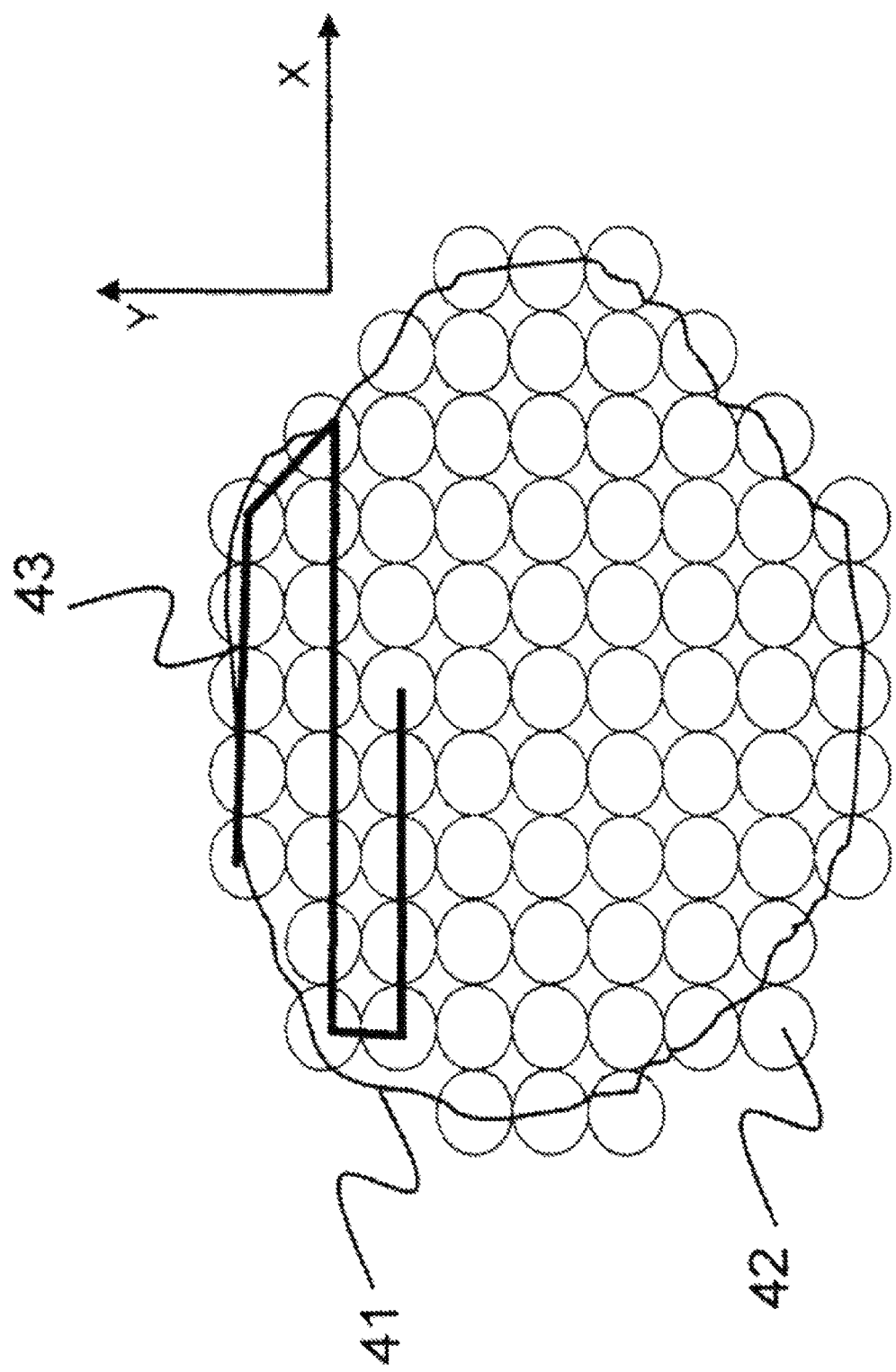
FIG. 3 is a diagram illustrating a specific layer of an affected part as an irradiation target in a depth direction.

A spot scanning method will be explained with reference to FIG. 2 and FIG. 3. FIG. 3 is a diagram illustrating a specific layer of the affected part 41 as the irradiation target in a depth direction, which is an explanatory drawing of the affected part 41 viewed from an upstream side of the charged particle beam.

As illustrated in FIG. 2, the shape of the affected part 41 of the patient 4 is divided into a plurality of layers in a three-dimensional depth direction, i.e. Z direction in FIG. 2. As illustrated in FIG. 3, each layer is further divided two-dimensionally in a horizontal direction, i.e. X-Y direction in FIG. 2 and FIG. 3, crossing a traveling direction of the charged particle beam, to set a plurality of dose divisions, which are small regions referred to as irradiation spots 42 hereinafter.

The depth direction corresponds to a reached depth of the charged particle beam. The charged particle beam extracted from the synchrotron 20 is changed by changing the energy of the charged particle beam, or by changing the energy of the charged particle beam through insertion of an energy absorber on an upstream side of the irradiator 500, or the like, and selectively irradiates each layer.

In each layer, for example, the charged particle beam is scanned two-dimensionally using the scanning magnets 51A and 51B along a pathway 43 illustrated in FIG. 3 to provide a prescribed dose to each irradiation spot 42. The dose of the charged particle beam irradiating each irradiation spot 42 is measured by the dose monitor 53A and the irradiation dose measurement device 53B, and the position and the extent, i.e. width, of the charged particle beam are measured by the beam position monitor 52A and the beam position measurement device 52B.

Irradiation control in accordance with the spot scanning technique is carried out by an irradiation controller 64 controlling the beam extraction from the charged particle beam generator 200.

As already explained, the spot scanning method is roughly divided into: a discrete spot scanning technique which is an irradiation technique in which irradiation with the charged particle beam is stopped while moving the position of the charged particle beam to the next irradiation spot 42; and a raster scanning technique which is an irradiation technique in which each irradiation spot 42 is irradiated with the charged particle beam only in a target dose, and then irradiation with the charged particle beam is not stopped even while moving the position of the charged particle beam to the next irradiation spot 42.

In the discrete spot scanning technique, beam extraction is stopped while moving the irradiation position of the charged particle beam from a lattice point to the next lattice point, and since beam extraction is restarted after completion of the movement, extraction of the charged particle beam is intermittent while scanning the same slice, i.e. layer.

Thus, when an irradiation dose of a charged particle beam irradiating one spot 42 among a plurality of irradiation spots 42 reaches a target dose, the irradiation controller 64 controls exciting currents of the scanning magnets 51A and 51B to scan the charged particle beam, and the irradiation position is changed to the next irradiation spot 42.

More specifically, when the irradiation dose of the charged particle beam irradiating one spot 42 reaches the target dose, the irradiation controller 64 stops extraction of the charged particle beam from the charged particle beam generator 200. Then, in a state in which the extraction of the charged particle beam is stopped, the irradiation controller 64 controls exciting currents of the scanning magnets 51A and 51B to scan the charged particle beam, and the irradiation position is changed to the next irradiation spot 42. After changing the irradiation position to the next irradiation spot 42, the irradiation controller 64 performs control so as to restart extraction of the charged particle beam from the charged particle beam generator 200.

Details of operations for the discrete spot scanning technique will be explained more specifically with reference to FIGS. 4A to 4F. FIGS. 4A to 4F are timing charts illustrating operations in a case of selecting the discrete spot scanning technique as an irradiation technique in the particle beam therapy system according to the embodiment. The timing charts of FIGS. 4A to 4F present operations while irradiating a certain layer in the affected part 41 illustrated in FIG. 3.

Figure 4:
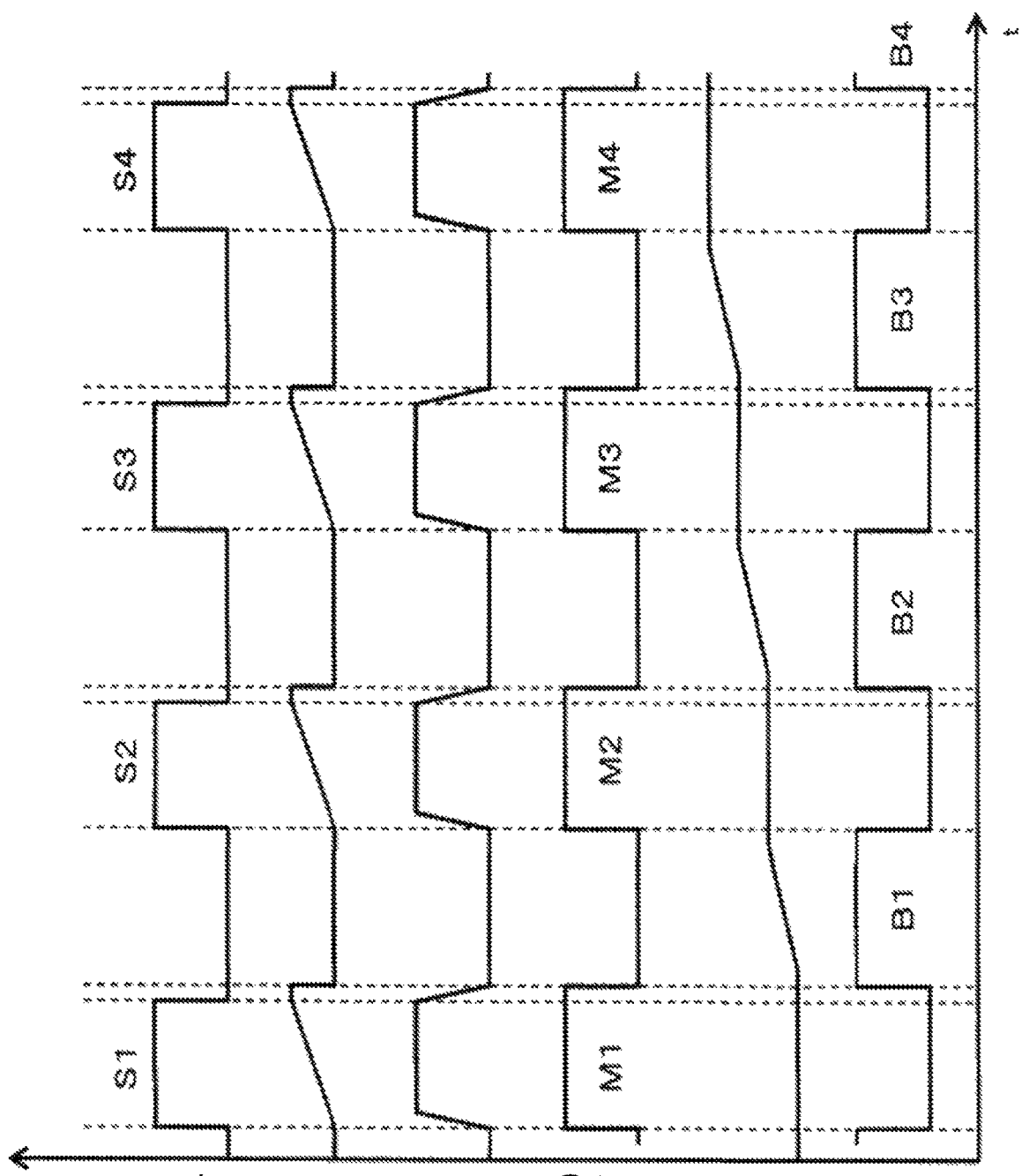
FIGS. 4A to 4F are timing charts illustrating operations in a case of selecting a discrete spot scanning technique as an irradiation technique in the particle beam therapy system according to the embodiment.

In FIGS. 4A to 4F, the abscissa indicates a time t, and the ordinate in FIG. 4A indicates opening/closing signals output from the irradiation controller 64 to the extraction switch 25 through a central control unit 65 and an accelerator controller 66, i.e. beam-ON/OFF signals controlling extraction of the charged particle beam. There are four ON states, i.e. four irradiation spots 42, in FIG. 4A, and therefore these spots are referred to as S1, S2, S3, and S4. Herein, after a doctor or a therapist gives instructions to start irradiation, when preparation for operation of the whole system including the charged particle beam generator 200 is completed through, for example, processes such as beam incidence and acceleration in the synchrotron 20, and the charged particle beam is ready to perform irradiation, a first beam-ON signal is generated.

The ordinate in FIG. 4B indicates a measured value obtained by measuring the irradiation dose of the charged particle beam u for irradiation using the dose monitor 53A and the irradiation dose measurement device 53B. As illustrated in FIG. 4B, the irradiation dose is integrated simultaneously with beam-ON switching, and the measurement signals are taken into the irradiation controller 64. When the integrated dose reaches a prescribed dose, the irradiation controller 64 switches off the beam, and the measured dose is stored in a memory of the irradiation controller 64. Then, the irradiation dose measurement device 53B is reset. Note that, although FIG. 4B illustrates that the irradiation dose measured by the dose monitor 53A and the irradiation dose measurement device 53B is reset at each irradiation spot 42, the irradiation dose may be determined by constantly integrating the doses at each irradiation spot and obtaining a difference in the integrated values.

The ordinate in FIG. 4C indicates an actual irradiation current of the charged particle beam. As illustrated in FIG. 4C, even after the dose reaches a prescribed dose illustrated in FIG. 4B and the beam is switched off, there is an OFF-reaction time, and therefore a minute amount of charged particle beam is provided for irradiation. In the discrete spot scanning technique, a leakage current is generated on each irradiation spot 42 due to a transient response after switching off the beam, and therefore the leakage current greatly affects application of a homogeneous dose, unless the extraction control of the accelerator and the extraction-ON/OFF response performance determined in the accelerator are at high levels.

The ordinate in FIG. 4D indicates a state of measurement by the beam position monitor 52A and the beam position measurement device 52B measuring the position and the width of the irradiation beam illustrated in FIG. 4C. For example, the irradiation controller 64 measures the irradiation spot S1, i.e. collects signals in an interval M1. After completing collection of signal from the beam position measurement device 52B illustrated in FIG. 4D, the irradiation controller 64 calculates the beam position and width, i.e. standard deviation, based on the acquired signals, and compares the position and width with permissible values previously set in the memory of the irradiation controller 64 to determine whether or not the values of the beam position/width are within desired error ranges.

When the calculation results of the beam position/width are determined as departing from the permissible values, the irradiation controller 64 generates interlock signals and stops progress to the next irradiation spot 42. For example, when the calculation results of the beam position/width at S1 on the irradiation spot 42 are determined as departing from the permissible values, progress is stopped at any timing before a predetermined period of time of the next interval S2.

In the discrete spot scanning technique, the irradiation beam current flows only during irradiation period at the irradiation spot and the subsequent response period, and monitor measurement is also carried out while the irradiation beam current flows. Thus, progress to the next irradiation spot 42 can be stopped with time to spare during the period in which no irradiation is carried out between the irradiation spots.

The ordinate in FIG. 4E indicates a current pattern of the power supply of scanning magnet 61 in a case where the charged particle beam is scanned two-dimensionally as illustrated in FIG. 3. This pattern is predetermined in the irradiation controller 64, and indicates an operation to sequentially change an excitation quantity and change the irradiation position after the irradiation dose at each irradiation spot 42 reaches a predetermined value and the irradiation beam is stopped.

The ordinate in FIG. 4F indicates a state of the power supply of scanning magnet 61. For the power supply of scanning magnet 61, the exciting current is changed, and while a current deviation departs from a desired range, the power supply of scanning magnet 61 is switched on. Such state is hereinafter referred to as "ON-scanning state." After the change of the exciting current is completed and the current deviation is determined as falling within the desired range, the power supply of scanning magnet 61 is switched off. Such state is hereinafter referred to as "OFF-scanning state." That means, after irradiating S1 in the irradiation spot 42 with the charged particle beam, the irradiation position is changed to the next irradiation spot 42 in an interval B1.

In FIG. 4F, a timing of starting irradiation of S2 in the irradiation spot 42 with the charged particle beam is when the irradiation position is changed after irradiating S1 in the irradiation spot 42 with the charged particle beam, i.e. when the ON-scanning state in FIG. 4F has been completed. Also after completion of the irradiation of S2 in the irradiation spot 42, the process flow after completion of the irradiation of S1 in the irradiation spot 42 with the charged particle beam is repeated, and two-dimensional scanning as illustrated in FIG. 3 progresses.

A series of operations in FIGS. 4A to 4F is repeated, and a specific layer of the affected part 41 in a depth direction illustrated in FIG. 3 is irradiated with the charged particle beam. The irradiation dose and the irradiation position of each irradiation spot 42, and the excitation quantity of the power supply of scanning magnet 61 corresponding to the irradiation dose and position follow a predetermined therapy plan. Before starting the therapy, contents of a therapy plan are transmitted from a therapy planning device 67 to the central control unit 65, and stored in the memory of the irradiation controller 64.

In the irradiation controller 64, an excitation pattern of the power supply of scanning magnet 61 is determined in accordance with the contents of the therapy plan. In addition, by the central control unit 65, an instruction for operating with an energy corresponding to a depth at which the affected part 41 is layeredly divided in the depth direction is transmitted to the accelerator controller 66 and a transporting system controller 68, and the accelerator controller 66 and the transporting system controller 68 perform the operation with the corresponding energy. Once the irradiation of one layer of the affected part 41 is completed, the central control unit 65 transmits an instruction for switching the energy so as to perform an operation with an energy corresponding to another layer. By repeating these steps, irradiation of the affected part 41 in whole is completed.

In contrast, in the raster scanning technique, extraction of the charged particle beam is continued without stop even while the irradiation position of the charged particle beam is moved from one irradiation spot 42 to the next irradiation spot 42. That means, while scanning the same slice, the extraction of the charged particle beam continues unremittingly.

Thus, when the irradiation dose of the charged particle beam irradiating one spot 42 among the plurality of irradiation spots 42 reaches the target dose, the irradiation controller 64 controls exciting currents of the scanning magnets 51A and 51B, scans the charged particle beam, and changes the irradiation position to the next irradiation spot 42. Even during this time, the irradiation controller 64 controls the exciting currents of the scanning magnets 51A and 51B and scans the charged particle beam, without pausing extraction of the charged particle beam from the charged particle beam generator 200, i.e. in a state in which the charged particle beam is extracted. Then the irradiation controller 64 performs controls in such a manner that the irradiation position is changed to the next irradiation spot 42.

Hereinafter, details of the raster scanning technique will be explained more specifically with reference to FIGS. 5A to 5E. FIGS. 5A to 5E are timing charts illustrating operations in a case of selecting the raster scanning technique as an irradiation technique in the particle beam therapy system 100 according to the embodiment. The timing chart of FIGS. 5A to 5E present operations while irradiating a certain layer in the affected part 41 illustrated in FIG. 3.

Figure 5:
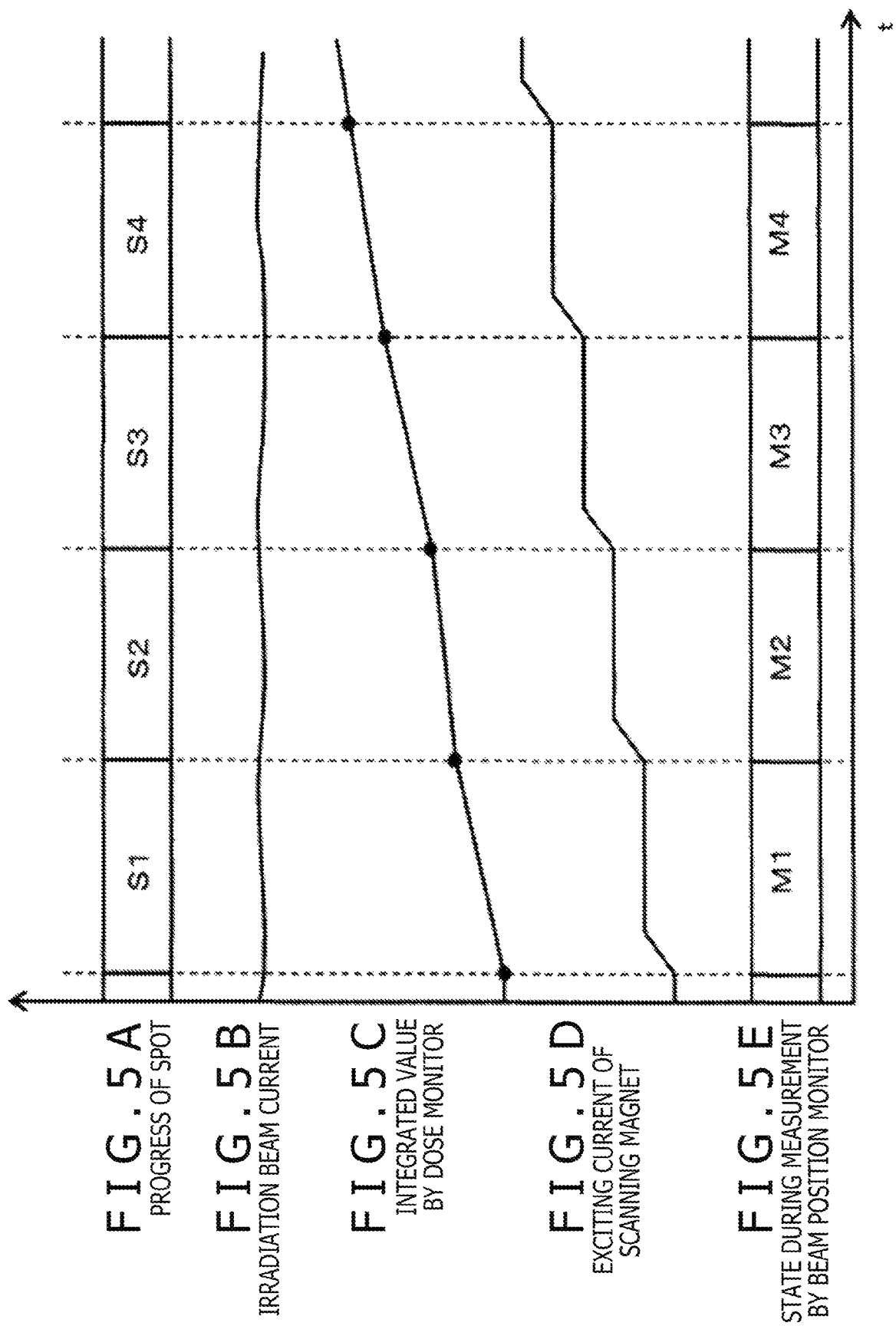
FIGS. 5A to 5F are timing charts illustrating operations in a case of selecting a raster scanning technique as an irradiation technique in the particle beam therapy system according to the embodiment.

In FIGS. 5A to 5F, the abscissa indicates a time t. FIG. 5A presents progress of the irradiation spot 42, and each interval S1, S2, S3, and S4 represents an interval of irradiation to each irradiation spot 42.

The ordinate in FIG. 5B indicates an irradiation current of the charged particle beam which is extracted from the charged particle beam generator 200 and enters the irradiator 500 through the beam-transporting system 300. In the raster scanning technique, the transient response associated to the beam-OFF occurs only at an end of the slice, i.e. layer, and therefore an influence from delay in the beam-OFF response is limited compared to the discrete spot scanning method.

The ordinate in FIG. 5C indicates an integrated value of doses measured by the dose monitor 53A and the irradiation dose measurement device 53B in the irradiator 500.

The ordinate in FIG. 5D indicates an exciting current of the power supply of scanning magnet 61. At the same time when the integrated irradiation dose illustrated in FIG. 5C reaches a planned dose prescribed for each spot, irradiation of the irradiation spot 42 is assumed to have been completed, and movement of the position of the charged particle beam to the next irradiation spot 42 is started.

Thus, first, the next irradiation spot 42 is irradiated while changing excitation quantities of the scanning magnets 51A and 51B. Then, after the change of the excitation quantities of the scanning magnets 51A and 51B is completed, the irradiation controller 64 stops the change of the excitation quantities of the scanning magnets 51A and 51B until the dose reaches the planned dose. Subsequently, at the same time when the irradiation dose reaches the planned value, the irradiation controller 64 repeats the operation of changing the exciting currents of the scanning magnets 51A and 51B for movement of the position of the charged particle beam to the next irradiation spot 42. Irradiation with the charged particle beam is also continued during the operation.

The ordinate in FIG. 5E indicates a measurement state of the beam position monitor 52A and the beam position measurement device 52B at each irradiation spot 42. As described above, in the interval M1 until the doses during scanning and during stop of scanning reach predetermined values, the beam position monitor 52A and the beam position measurement device 52B measure the beam position at each irradiation spot 42.

After completing collection of signal from the beam position measurement device illustrated in FIG. 5E, the irradiation controller 64 calculates the beam position and width, i.e. standard deviation, based on acquired signals, and compares the beam position and width with the permissible values previously set in the memory of the irradiation controller 64 to determine whether or not the values of the beam position/width are within desired error ranges.

In FIGS. 5A to 5E, a timing of starting the irradiation of S2 in the irradiation spot 42 is after the irradiation of S1 in the irradiation spot 42 is completed. Also after completion of the irradiation of S2 in the irradiation spot 42, the process flow after completion of the irradiation of S1 in the irradiation spot 42 with the charged particle beam is repeated, and two-dimensional scanning as illustrated in FIG. 3 progresses.

Also when repeating the series of operations in FIGS. 5A to 5E, a specific layer of the affected part 41 in a depth direction illustrated in FIG. 3 is irradiated with the charged particle beam in accordance with the therapy plan, in the same manner as the series of repeated operations from FIGS. 4A to 4F.

In this raster scanning technique, a timing of stopping irradiation with the charged particle beam is when the interval between the irradiation spots 42 becomes large during irradiation of a certain layer of the affected part 41 illustrated in FIG. 3, during which the irradiation dose becomes too large to be negligible. In addition, irradiation with the charged particle beam is also stopped when irradiation of a certain layer illustrated in FIG. 3 with the charged particle beam is completed and the irradiation layer is changed to another layer in another depth, i.e. when an energy of the charged particle beam entering the irradiator 500 is changed, and also when unacceptable factors for pausing the beam are caused.

In both irradiation control techniques, in the irradiation controller 64, the irradiation controller 64 reads out signals obtained from the beam position monitor 52A and the beam position measurement device 52B, and then calculates the beam position and width to determine whether calculated values of the position/width of this charged particle beam depart from the permissible values. When the calculated values of the position/width of the charged particle beam depart from the permissible values, an interlock signal is output to the accelerator controller 66 via the central control unit 65, to stop extraction of the charged particle beam from the charged particle beam generator 200.

In the particle beam therapy system 100 according to the present embodiment, it is possible to select either the raster scanning technique or the discrete spot scanning technique, based on previous selection, depending on the affected part 41 of the patient 4 as an irradiation target. Furthermore, both the raster scanning technique and the discrete spot scanning technique are configured to be executed by one common charged particle beam generator 200, one common beam-transporting system 300, one common irradiator 500, and controller 600 many of whose components are common.

Hereinafter, a configuration for the irradiation techniques will be explained.

As illustrated in FIG. 1, the controller 600 is an apparatus controlling each device in the synchrotron 20, the beam-transporting system 300 and the irradiator 500, and includes the accelerator controller 66, the irradiation controller 64, the central control unit 65, the transporting system controller 68, and a therapy planning device 67.

The controller 600 is an information processor including a calculation section having an arithmetic element such as central processing unit (CPU), a memory section having a memory medium such as flash memory device and hard disk drive (HDD), and an input/output section which is operated by a maintenance staff or the like for the particle beam therapy system 100 and has a keyboard, a mouse, a display, and the like. When the controller 600 is turned on, the calculation section reads out and executes a program such as a firmware stored in the memory section, and thereby, functions as the accelerator controller 66, the irradiation controller 64, the central control unit 65, the transporting system controller 68, and the therapy planning device 67 are effected.

The accelerator controller 66, the irradiation controller 64, the central control unit 65, the transporting system controller 68, and the therapy planning device 67 which constitute the controller 600 may be effected by one information processor, or alternatively, some devices such as the accelerator controller 66 may be effected by a separate information processer.

The therapy planning device 67 is a device which prepares a plan for irradiation with a charged particle beam. Based on the information about the affected part 41 of the patient 4 as an irradiation target, the therapy planning device 67 selects either the raster scanning technique or the discrete spot scanning technique for therapy and prepares the therapy plan. The therapy planning device 67 outputs the prepared therapy plan to the central control unit 65.

Based on the therapy plan input from the therapy planning device 67, the central control unit 65 outputs control signals to each controller, i.e. the accelerator controller 66, the irradiation controller 64, and the transporting system controller 68 so as to control irradiation of the affected part 41 of the patient 4 using either the raster scanning technique or the discrete spot scanning technique.

The control signals output to the accelerator controller 66, the irradiation controller 64 and the like from the central control unit 65 include control data, i.e. control parameter set, required for operations of these accelerator controller 66 and the like. The control data includes common control section-controlling data for common control sections 64a and 66a used in both irradiation techniques, non-stop control section-controlling data for non-stop control sections 64b and 66b used only in the raster scanning technique, and stop control section-controlling data for stop control sections 64c and 66c used only in the discrete spot scanning technique.

The central control unit 65 includes: a display section 65a displaying which irradiation technique has been selected from the raster scanning technique and the discrete spot scanning technique; and an input section, i.e. input device, 65b which receives a technique-switching input for either the raster scanning technique or the discrete spot scanning technique, input by a maintenance staff or the like for the particle beam therapy system 100. In addition, the input section 65b receives a mode-switching-instructing input between a therapy irradiation mode irradiating the affected part 41 with the particle beam and a verification irradiation mode for tentative irradiation with the particle beam, input by a maintenance staff or the like for the particle beam therapy system 100.

The accelerator controller 66 includes the common control section 66a used in both irradiation techniques, the non-stop control section 66b used only in the raster scanning technique, and the stop control section 66c used only in the discrete spot scanning technique. The accelerator controller 66 controls each device such as the synchrotron 20 in the charged particle beam generator 200.

In the accelerator controller 66, based on the control signal from the central control unit 65, in a case of irradiation in the raster scanning technique, control is carried out by the common control section 66a and the non-stop control section 66b and in a case of irradiation in the discrete spot scanning technique, control is carried out by the common control section 66a and the stop control section 66c.

For example, the common control section 66a performs control using the common control section-controlling data which is common between the discrete spot scanning technique and the raster scanning technique. This common control section-controlling data is used to control the pre-stage accelerator 21, the dipole magnet 22, and the accelerator 23 when the particles entering from the prestage accelerator 21 are accelerated in the synchrotron 20, which is common between the controls in both techniques.

The non-stop control section 66b performs control using the non-stop control section-controlling data used only in the raster scanning technique. This non-stop control section-controlling data is used when controlling the extraction device 24 and the extraction switch 25.

The stop control section 66c performs control using the stop control section-controlling data used only in the discrete spot scanning technique. This stop control section-controlling data is used when controlling the extraction device 24 and the extraction switch 25. Incidentally, for controlling equipment such as electromagnets for extraction, and beam extraction which are common between both techniques, it is necessary to achieve a beam current response speed satisfying requirements for the discrete spot scanning technique.

Also, the accelerator controller 66 can control both techniques in one common control section by applying the stop control section 66c corresponding to the discrete spot scanning technique to irradiation in the raster scanning technique. In this case, irradiation in the raster scanning technique is controlled so that the beam is kept in an ON-state until irradiation of a slice is completed although normally the stop control section 66c transmits a beam-OFF signal when the irradiation dose reaches a predetermined value.

The irradiation controller 64 includes the common control section 64a used in both irradiation techniques, the non-stop control section 64b used only in the raster scanning technique, and the stop control section 64c used only in the discrete spot scanning technique. The irradiation controller 64 controls each device in the irradiator 500.

Based on the control signal from the central control unit 65, in a case of irradiation in the raster scanning technique, the irradiation controller 64 performs control using the common control section 64a and the non-stop control section 64b, and in a case of irradiation in the discrete spot scanning technique, the irradiation controller 64 performs control using the common control section 64a and the stop control section 64c.

For example, the common control section 64a performs control using the common control section-controlling data which is common between the discrete spot scanning technique and the raster scanning technique. The common control section-controlling data is used, for example, for controlling the power source of the power supply of scanning magnet 61 which is common between both techniques.

The non-stop control section 64b performs control using the non-stop control section-controlling data used only in the raster scanning technique. The stop control section 64c performs control using the stop control section-controlling data used only in the discrete spot scanning technique. These non-stop control section-controlling data and stop control section-controlling data control, for example, the beam position measurement device 52B and the irradiation dose measurement device 53B for which timings and control methods are different between the two techniques.

The transporting system controller 68 controls each of the equipment such as the dipole magnet 31 in the beam-transporting system 300.

Next, operation of the controller 600 of the present example will be explained with reference to the flowcharts in FIG. 6 and FIG. 7, and the diagrams in FIG. 8 to FIG. 11.

Figure 6:
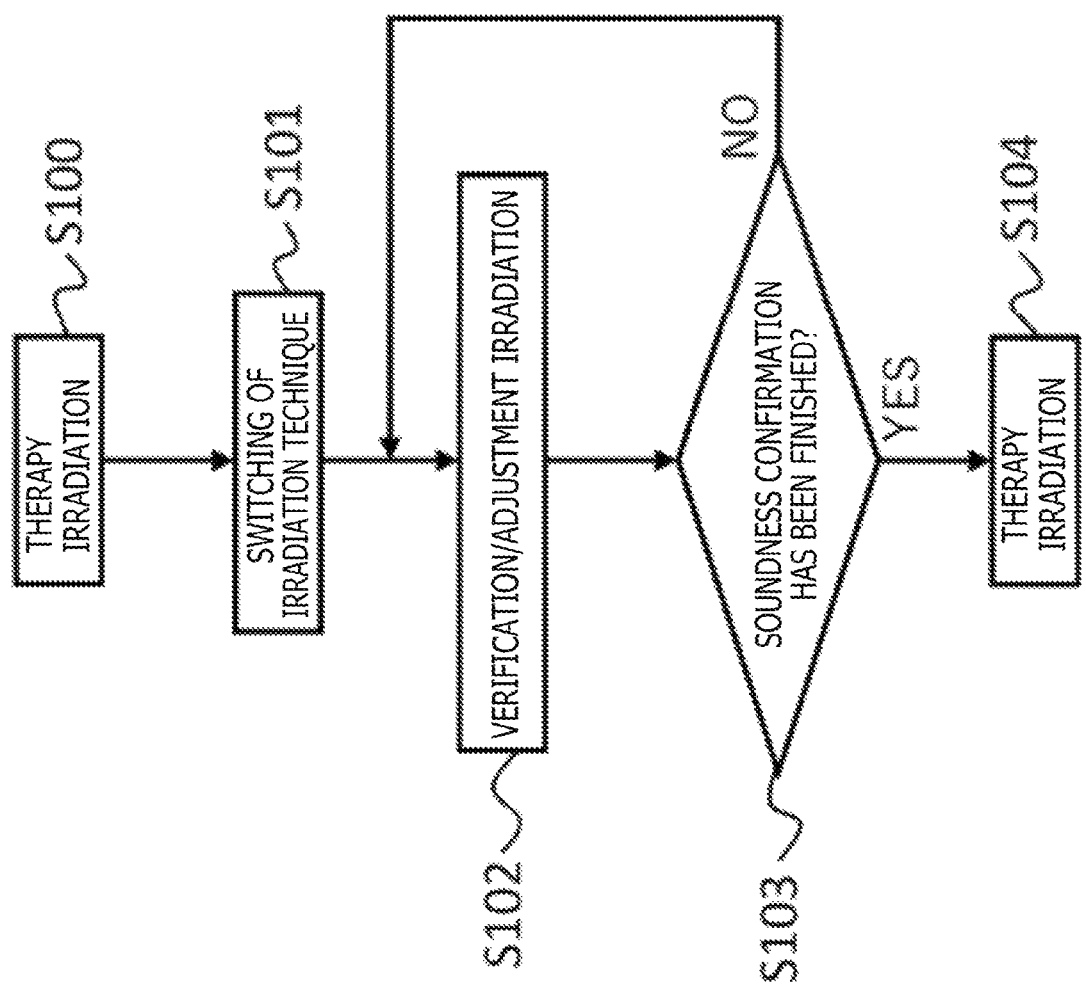
FIG. 6 is a flowchart explaining an irradiation technique-switching operation in the particle beam therapy system according to the embodiment.

FIG. 6 is a flowchart for explaining an irradiation technique-switching operation in the particle beam therapy system 100 according to the embodiment.

In either the raster scanning technique or the discrete spot scanning technique, the particle beam therapy system 100 performs one therapy by irradiating the affected part 41 of the patient 4 with the charged particle beam (step S100).

Subsequently, for the purpose of treating an affected part 41 of another patient 4 or another affected part 41 of the same patient 4 with the charged particle beam, the therapy planning device 67 prepares a therapy plan. The therapy plan prepared by the therapy planning device 67 is output to the central control unit 65.

When the irradiation technique of the charged particle beam should be switched, a maintenance staff performs a switching input for the irradiation technique by the input section 65b of the central control unit 65 based on the therapy plan prepared by the therapy planning device 67, in a time period during which no therapy irradiation is carried out (step S101).

Before shifting to the next therapy irradiation, the central control unit 65 performs verification/adjustment irradiation to accurately verify soundness of the particle beam therapy system 100 regarding switching of the control data, i.e. control parameter set (step S102).

The central control unit 65 determines whether or not the soundness after switching the irradiation technique could be confirmed by the verification/adjustment irradiation (step S103), and only when the soundness could be confirmed ("YES" in step S103), therapy irradiation is carried out by the particle beam therapy system 100 after switching the irradiation technique (step S104).

Incidentally, since the therapy planning device 67 designates an irradiation technique depending on the affected part 41 of the patient 4 as an irradiation target, this verification/adjustment irradiation may be carried out during one therapy irradiation.

FIG. 7 is a flowchart for explaining an operation of the verification/adjustment irradiation in the particle beam therapy system 100 according to the embodiment.

The central control unit 65 has two types of irradiation modes: a therapy irradiation mode irradiating the affected part 41 of the patient 4 with the charged particle beam; and a verification/adjustment irradiation mode for tentative irradiation with the charged particle beam. Switching between the therapy irradiation mode and the verification/adjustment irradiation mode is carried out by a maintenance staff using the input section 65b of the central control unit 65 (step S200). The switched irradiation mode is displayed on the display section 65a of the central control unit 65. Switching is carried out using a display.

When switching is carried out between the therapy irradiation mode and the verification/adjustment irradiation mode in step S200, an instruction for switching the irradiation mode is output to the accelerator controller 66, the irradiation controller 64, and the transporting system controller 68 from the central control unit 65 (step S201).

The accelerator controller 66, the irradiation controller 64, and the transporting system controller 68 switch the irradiation mode based on the instruction for switching to the irradiation mode output from the central control unit 65, and then information about which irradiation mode is currently set is output to the central control unit 65 (step S202). Based on information output from the accelerator controller 66 and the like, the central control unit 65 confirms whether the irradiation mode has been switched reliably.

Subsequently, a maintenance staff or the like for the particle beam therapy system 100 sets the control data for the verification/adjustment irradiation mode using the input section 65b and the display section 65a of the central control unit 65 (step S203). Then, the central control unit 65 transmits the control data set in step S203 to the accelerator controller 66, the irradiation controller 64, and the transporting system controller 68 (step S204). Following this, when transmitting the control data, the central control unit 65 outputs a control signal indicating either the raster scanning technique or the discrete spot scanning technique, to the accelerator controller 66, the irradiation controller 64, and the transporting system controller 68 (step S206).

The accelerator controller 66, the irradiation controller 64, and the transporting system controller 68 store the irradiation mode, the control data and the irradiation technique received from the central control unit 65 in memories housed in these accelerator controller 66 and the like. By the accelerator controller 66, the irradiation controller 64, and the transporting system controller 68 which have received the irradiation technique, the irradiation mode, the control data, and the irradiation technique read from the memories are transmitted to the central control unit 65 (steps S202, S205 and S207).

The central control unit 65 determines whether or not the irradiation mode, the control data, and the irradiation technique it transmitted accord with the irradiation mode, the control data, and the irradiation technique received from the accelerator controller 66, the irradiation controller 64, and the transporting system controller 68 (step S208). If it is determined that they accord with each other ("YES" in step S208), the process proceeds to step S209. On the other hand, if it is determined that they do not accord with each other, i.e., there is no consistency ("NO" in step S208), the process returns to step S203, and the maintenance staff or the like sets the control data for the verification/adjustment irradiation mode again.

When the central control unit 65 determines that the irradiation mode, the control data, and the irradiation technique it transmitted accord with the irradiation mode, the control data, and the irradiation technique received from the accelerator controller 66, the irradiation controller 64, and the transporting system controller 68, the central control unit 65 outputs an irradiation enable signal to the accelerator controller 66, the irradiation controller 64, and the transporting system controller 68 (step S209). This makes it possible to perform irradiation with the charged particle beam in the verification/adjustment irradiation mode.

After that, the maintenance staff for the particle beam therapy system 100 causes the particle beam therapy system 100 to perform irradiation with the charged particle beam (step S210). The central control unit 65 monitors the irradiation dose measured by the irradiation dose measurement device 53B to determine whether or not irradiation at the irradiation dose set as the control data in step S203 has been performed normally (step S211). If it is determined that irradiation at the set irradiation dose has not been performed normally ("NO" in step S211), the central control unit 65 determines abnormality in soundness and prevents the process from shifting to the therapy irradiation. That means, the central control unit 65 has an interlock function.

This interlock becomes valid at the time when an operator switches the irradiation technique (step S200), and thereafter, the interlock continues to be valid until irradiation at the irradiation dose is performed normally in the verification/adjustment irradiation mode ("YES" in step S211). While the interlock is valid, the display section 65a of the central control unit 65 displays that the interlock is valid, to alert the operator.

Although not explicitly described in the flowchart in FIG. 7, at the time of irradiation with the charged particle beam in the verification/adjustment irradiation mode, the central control unit 65 determines whether calculated values of the position/width of the charged particle beam is based on the control data set in step S203, by the beam position measurement device 52B and the irradiation dose measurement device 53B. Then, if the calculated values of the position/width of the charged particle beam depart from the values based on the control data, the central control unit 65 discontinues irradiation with the charged particle beam, and returns the process to step S203, and the maintenance staff or the like sets the control data for the verification/adjustment irradiation mode again.

If it is determined that irradiation at the irradiation dose has been performed normally in the verification/adjustment irradiation mode ("YES" in step S211), the central control unit 65 unlocks the interlock function which prevents the process from shifting to the therapy irradiation (step S212). Then, the central control unit 65 allows the therapy irradiation in accordance with one of the irradiation techniques switched (step S213).

Figure 8:
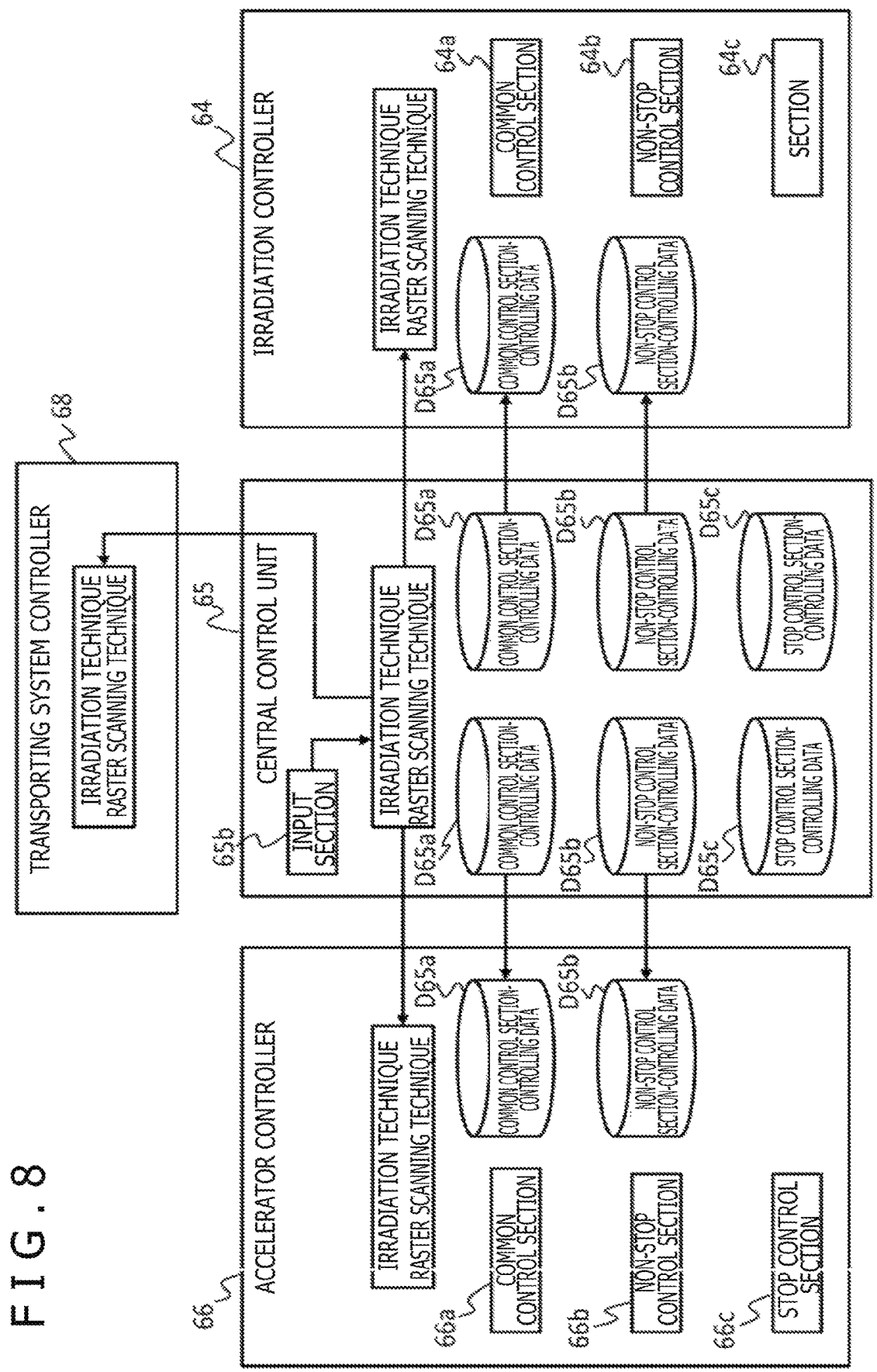
FIG. 8 is a diagram illustrating one example of a data flow in a case of selecting the raster scanning technique in the particle beam therapy system according to the embodiment.

FIG. 8 is a diagram illustrating one example of a data flow in a case of selecting the raster scanning technique in the particle beam therapy system 100 according to the embodiment.

Prior to the therapy irradiation, from the central control unit 65, either the raster scanning technique or the discrete spot scanning technique designated by the input section 65b, i.e. the raster scanning technique in FIG. 8, is output to the transporting system controller 68, the accelerator controller 66 and the irradiation controller 64, as a control signal. Furthermore, from the central control unit 65, common control section-controlling data D65a used for control and non-stop control section-controlling data D65b as raster scanning-controlling data are transmitted to the accelerator controller 66 and the irradiation controller 64. In such a way, the central control unit 65 centrally manages the irradiation technique and outputs the irradiation technique, as a control signal, to each controller 64, 66, and 68, so that it becomes unnecessary to switch the setting for each controller, and erroneous irradiation with a particle beam due to discordant switching for setting can be prevented.

Figure 9:
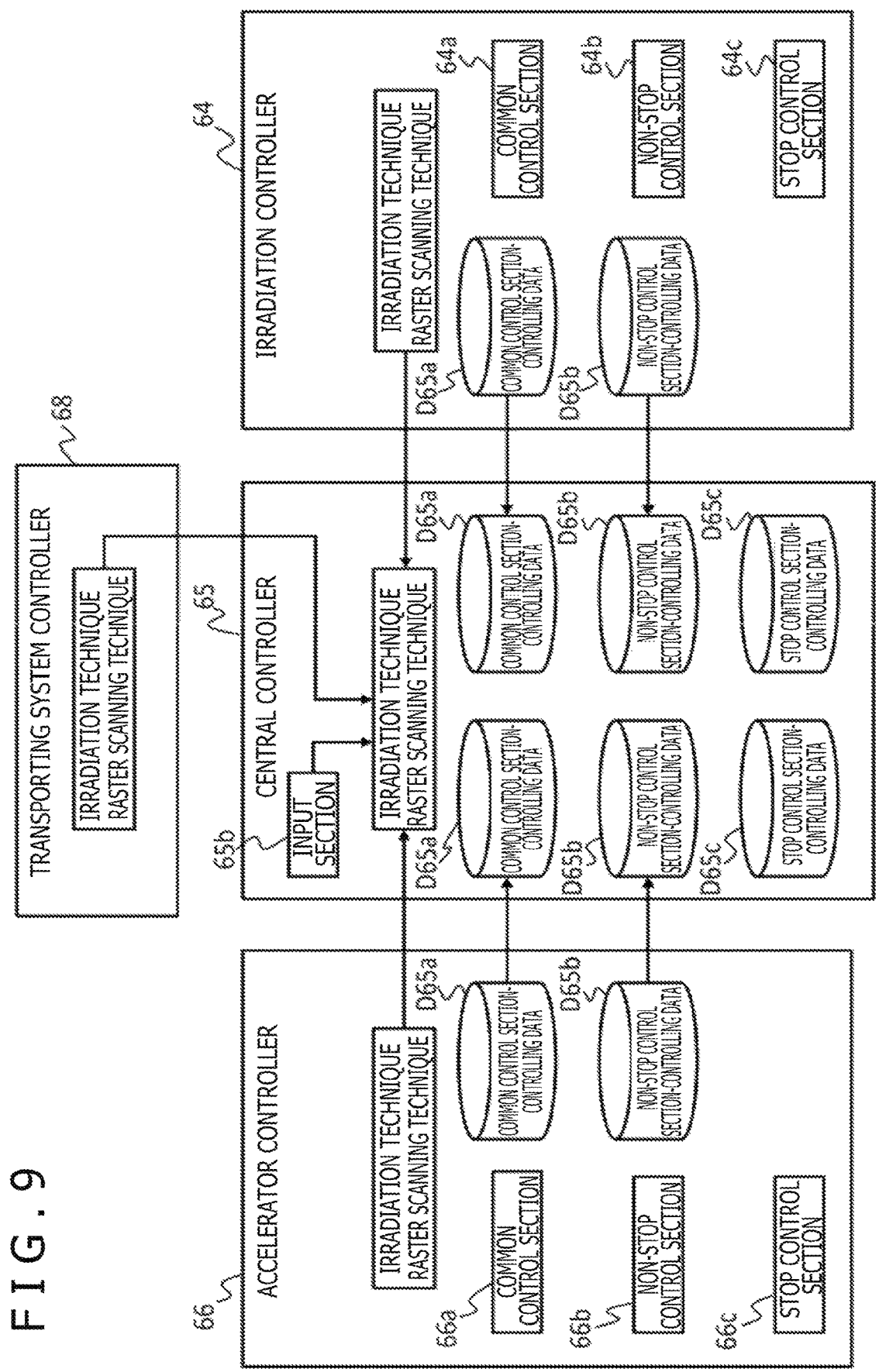
FIG. 9 is a diagram illustrating another example of a data flow in a case of selecting the raster scanning technique in the particle beam therapy system according to the embodiment.

FIG. 9 is a diagram illustrating another example of a data flow in a case of selecting the raster scanning technique in the particle beam therapy system 100 according to the embodiment.

FIG. 9 illustrates a procedure for confirming whether the irradiation technique output from the central control unit 65 has been accepted by the accelerator controller 66, the irradiation controller 64, and the transporting system controller 68, and the irradiation technique has been selected correctly.

By the accelerator controller 66, the irradiation technique, the common control section-controlling data D65a, and the non-stop control section-controlling data D65b which have been received from the central control unit 65 are transmitted to the central control unit 65. The central control unit 65 confirms whether the irradiation technique and the like transmitted to the accelerator controller 66 accord with the irradiation technique and the like received from the accelerator controller 66. When discordance is detected in the irradiation technique or the like, the central control unit 65 outputs a message to the display section 65a, and switches off the particle beam irradiation enable signal to preclude irradiation with the charged particle beam.

In addition, by the irradiation controller 64, the irradiation technique, the common control section-controlling data D65a, and the non-stop control section-controlling data D65b which are received from the central control unit 65 are transmitted to the central control unit 65. The central control unit 65 confirms whether the irradiation technique and the like transmitted to the irradiation controller 64 accord with the irradiation technique and the like received from the irradiation controller 64. When discordance is detected in the irradiation technique or the like, the central control unit 65 outputs a message to the display section 65a, and switches off the particle beam irradiation enable signal to preclude irradiation with the charged particle beam.

Furthermore, by the transporting system controller 68, the irradiation technique received from the central control unit 65 is transmitted to the central control unit 65. The central control unit 65 confirms whether the irradiation technique transmitted to the transporting system controller 68 accords with the irradiation technique received from the transporting system controller 68. When discordance is detected in the irradiation technique, the central control unit 65 outputs a message to the display section 65a, and switches off the particle beam irradiation enable signal to preclude irradiation with the charged particle beam.

In such a way, the central control unit 65 checks matching between the transmission data and the reception data of the irradiation technique and the control data to reliably detect abnormality. In addition, when discordance is detected, the central control unit 65 precludes irradiation with the charged particle beam to prevent irradiation with the charged particle beam in an irradiation technique different from the set irradiation technique.

Figure 10:
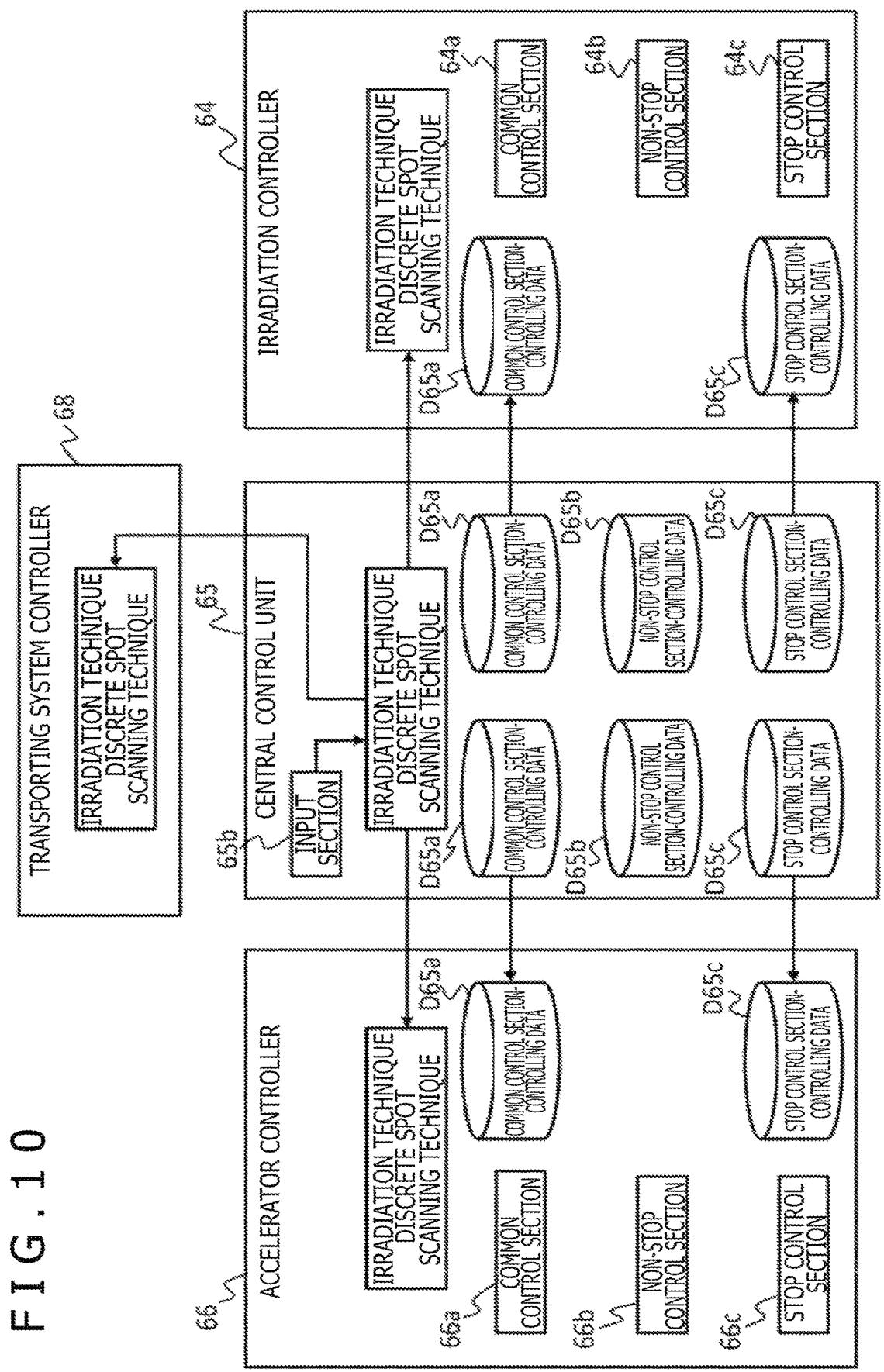
FIG. 10 is a diagram illustrating one example of a data flow in a case of selecting the discrete spot scanning technique in the particle beam therapy system according to the embodiment.

FIG. 10 is a diagram illustrating one example of a data flow in a case of selecting the discrete spot scanning technique in the particle beam therapy system 100 according to the embodiment.

In the example illustrated in FIG. 10, prior to the therapy irradiation, by the central control unit 65, the discrete spot scanning technique as an irradiation technique designated by the input section 65b is output to the transporting system controller 68, the accelerator controller 66 and the irradiation controller 64, as a control signal. Furthermore, by the central control unit 65, the common control section-controlling data D65a used for control and stop control section-controlling data D65c as discrete spot scanning-controlling data are transmitted to the accelerator controller 66 and the irradiation controller 64.

Figure 11:
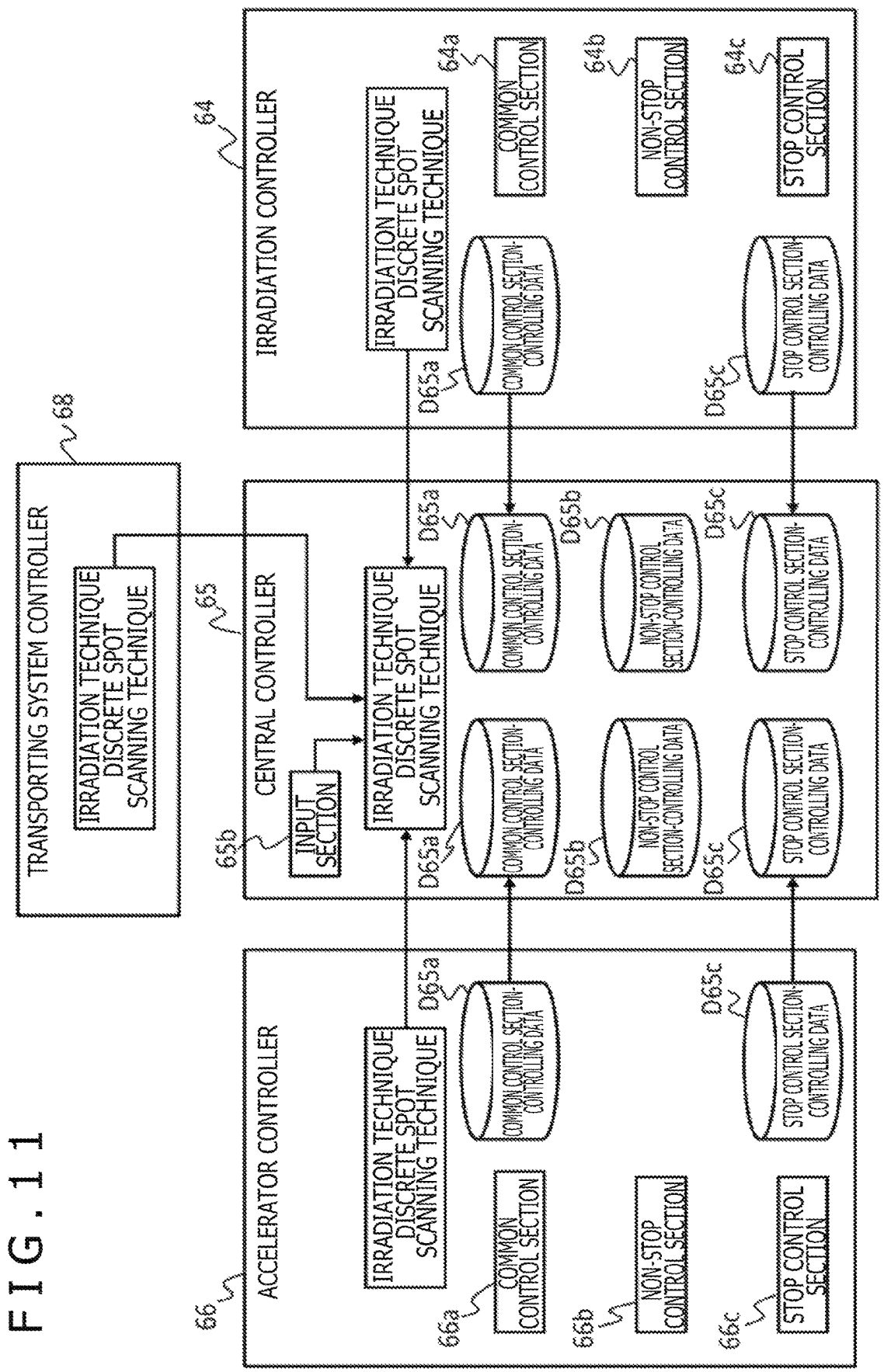
FIG. 11 is a diagram illustrating another example of a data flow in a case of selecting the discrete spot scanning technique in the particle beam therapy system according to the embodiment.

FIG. 11 is a diagram illustrating another example of a data flow in a case of selecting the discrete spot scanning technique in the particle beam therapy system 100 according to the embodiment.

The example illustrated in FIG. 11 is different from the example illustrated in FIG. 9 only in that the irradiation technique, the common control section-controlling data D65a and the stop control section-controlling data D65c received from the central control unit 65 are transmitted from the accelerator controller 66 and the irradiation controller 64 to the central control unit 65. Since the other operations are the same as in the example illustrated in FIG. 9, explanations of the other operations are omitted in the specification.

Incidentally, if the therapy irradiation is carried out without switching the irradiation technique, the therapy irradiation is repeated without performing irradiation in the verification/adjustment irradiation mode.

According to the present example configured as described above, the charged particle beam generator 200, the beam-transporting system 300 and the irradiator 500 are controlled so that the controller 600 switches between the two irradiation techniques, i.e. the raster scanning technique and the discrete spot scanning technique, to irradiate the target with the particle beam. Furthermore, after switching the irradiation technique, tentative irradiation with the particle beam is performed by the charged particle beam generator 200, the beam-transporting system 300 and the irradiator 500 in the switched irradiation technique, and this particle beam is verified.

Consequently, according to the present example, a particle beam therapy system 100 and a particle beam therapy method which can reliably verify irradiation with a particle beam in accordance with a selected irradiation technique can be achieved. Furthermore, the particle beam therapy system 100 and the particle beam therapy method according to the present example make it possible to accurately verify soundness of switching of the irradiation technique.

In addition, the particle beam therapy system 100 according to the present embodiment can achieve both irradiation techniques, i.e. the raster scanning technique and the discrete spot scanning technique, in one irradiator 500 while the basic apparatus configurations for the two irradiation techniques are the same. This makes it possible to select an appropriate technique depending on the irradiation target, so that both improvement of irradiation accuracy and increase of a dose rate can be achieved, and various advantages such as shortened irradiation time can be obtained.

For example, when an affected part of a childhood cancer or the like is irradiated while observing movement of the affected part with an X-ray and synchronizing the irradiation with the movement, highly accurate irradiation is carried out in a discrete spot scanning technique. In addition, when movement of an affected part of a prostate cancer or the like is small, the irradiation time can be shortened by irradiating continuously for a long period of time in the raster scanning technique. In addition, there are advantages that the system is inexpensive and the therapy system can be downsized because both irradiation techniques can be achieved by one system.

Modifications

Incidentally, the present invention is not limited to the aforementioned examples, and includes various modifications. For example, the aforementioned examples have been explained in detail for the purpose of clarifying the present invention, and are not necessarily limited to examples having all configurations explained above. In addition, a part of a configuration of an example can be replaced by a configuration of another example, and a configuration of an example can be added to a configuration of another example. Furthermore, a part of the configuration of each example can be added with or replaced with another configuration, or deleted.

As an example, a case using the extraction device 24 having the high frequency applying electrode for extraction as a beam discharger has been explained, but the beam discharger is not limited to the extraction device 24, and a quadrupole electromagnet for extraction, a betatron core, or the like may be used.

In addition, each of the aforementioned configurations, functions, processing sections, processing means, and the like may be achieved on a hardware by, for example, designing, in whole or in part, the configurations, functions, processing sections, processing means and the like using, for example, an integrated circuit. In addition, each of the aforementioned configurations, functions and the like may be achieved using software by interpreting and executing a program in which each function is effected by a processor. Information such as programs, tables, and files for effecting each function can be stored in a recorder such as a memory, a hard disk and an SSD, or recording medium such as an integrated circuit (IC) card, a secure digital (SD) card and a digital versatile disc (DVD).

In addition, for the control lines and information lines, lines considered necessary for explanation are illustrated, and all the control lines and information lines on the product are not necessarily illustrated. It may also be considered that almost all the configurations are actually connected to each other.

What is claimed is:

1. A particle beam therapy system comprising:
    an accelerator accelerating a particle beam,
    an irradiator irradiating a target with the particle beam accelerated by the accelerator, and
    a controller controlling the accelerator and the irradiator,
    wherein the controller controls the accelerator and the irradiator so as to irradiate the target with the particle beam through switching between at least two different irradiation techniques, and furthermore, after switching between the irradiation techniques, controls the accelerator and the irradiator so as to perform tentative irradiation with the particle beam in accordance with one of the irradiation techniques switched, to verify the particle beam, wherein an input device is provided, the input device receiving a mode-switching-instructing input for switching to a therapy irradiation mode of irradiating the target with the particle beam and other mode-switching instructing input for switching to a verification irradiation mode for tentative irradiation with the particle beam, wherein the controller controls the accelerator and the irradiator so as to perform irradiation with the particle beam based on one of the mode-switching-instructing inputs received by the input device, wherein the irradiator has an irradiation dose measurement device measuring an irradiation dose of the particle beam used for irradiation, and wherein once starting irradiation with the particle beam in accordance with the verification irradiation mode, the controller does not receive the mode-switching-instructing input for switching to the therapy irradiation mode until a prescribed irradiation dose is measured by the irradiation dose measurement device.

2. The particle beam therapy system according to claim 1, wherein once receiving the other mode-switching-instructing input for switching to the verification irradiation mode, the controller does not receive the mode-switching-instructing input for switching to the therapy irradiation mode until a prescribed irradiation dose is measured by the irradiation dose measurement device.

3. A particle beam therapy system comprising:
an accelerator accelerating a particle beam,
an irradiator irradiating a target with the particle beam accelerated by the accelerator, and
a controller controlling the accelerator and the irradiator,
wherein the controller controls the accelerator and the irradiator so as to irradiate the target with the particle beam through switching between at least two different irradiation techniques, and furthermore, after switching between the irradiation techniques, controls the accelerator and the irradiator so as to perform tentative irradiation with the particle beam in accordance with one of the irradiation techniques switched, to verify the particle beam, wherein
the controller includes an accelerator controller controlling the accelerator, an irradiation controller controlling the irradiator, and a central control unit controlling the accelerator controller and the irradiation controller,
when switching the irradiation techniques, by the central control unit, control data used for the irradiation techniques to be switched is transmitted to the accelerator controller and the irradiation controller,
once receiving the control data from the central control unit, the accelerator controller and the irradiation controller each transmits verification data of the received control data to the central control unit, and
once receiving verification data from each of the accelerator controller and the irradiation controller, the central control unit confirms consistency between the verification data and the control data transmitted to the accelerator controller and the irradiation controller, and prevents irradiation with the particle beam until confirmation of the consistency is completed.

* * * * *